United States Patent [19]

Welle et al.

[11] 4,085,225

[45] Apr. 18, 1978

[54] OXIME ETHERS HAVING ANTI-DEPRESSIVE ACTIVITY

[75] Inventors: Hendricus Bernardus Antonius Welle, Utrecht; Volkert Claassen, Weesp, both of Netherlands

[73] Assignee: U.S. Philips Corporation, New York, N.Y.

[21] Appl. No.: 668,461

[22] Filed: Mar. 19, 1976

[30] Foreign Application Priority Data

Mar. 20, 1975 Netherlands .......................... 7503310

[51] Int. Cl.$^2$ ................... A61K 31/15; A61K 31/275; C07C 121/78; C07C 131/00
[52] U.S. Cl. ................................ 424/304; 260/465 E; 260/501.17; 260/566 AE; 424/316; 424/327
[58] Field of Search .................... 260/465 E, 566 AE; 424/304, 327

[56] References Cited

U.S. PATENT DOCUMENTS 3,692,835   9/1972   Van Dijk et al. ............. 260/566 AE

*Primary Examiner*—Dolph H. Torrence
*Attorney, Agent, or Firm*—Frank R. Trifari; Norman N. Spain

[57] ABSTRACT

Novel 4'-trifluoromethylvalerophenone O-(2-aminoethyl)oximes are found to exhibit a strong anti-depressive activity based on a strong serotone potentiation but with the absence of monoamino/oxidase inhibition and undesirable side effects.

8 Claims, No Drawings

OXIME ETHERS HAVING ANTI-DEPRESSIVE ACTIVITY

The invention relates to novel oxime ether compounds having anti-depressive activity. In British Patent Specification No. 1,205,665, a large group of compounds is described as having an anti-depressive, a sedative and/or an anti-convulsive activity. The anti-depressive activity of the known compounds according to this Patent Specification is based on monoamino oxidase (MAO) inhibition and/or on noradrenaline potentiation.

Compounds which inhibit monoamino oxidase are particularly difficult to administer. They often have serious side effects and they are often incompatible with other medicines and nutrients. As the regulations governing the use of medicines become more and more stringent only certain compounds which are substantially free from noxious side effects can be considered for administration to human beings.

It is the object of the invention to provide novel anti-depressive agents whose activity component is not based on MAO inhibition and which in addition are substantially free from side effects and whose action is primarily expressed in an elevation of mood of the treated patient and to a much smaller extent in an increase of the motor activity.

Prior biochemical investigations in depressive patients, Brit. J. Phychiatr. 113 1407 (1967); Nature 225 1259 (1970); and Arch. Gen. Psychiatr. 28 827 (1973) have lent support to the hypothesis that a decrease of the serotonergic processes in the brains is a factor in the pathogenesis of depressions.

However, investigations in other patients do not lead to this supposition, Arch. Gen. Psychiatr. 25 354 (1971). Therefore, a current opinion, which is gaining support, is that there are various "sub-types" classifications of patients whose depressions are caused by different deviations in the metabolism of biogenic amines. This may account for the fact why patients who fall into these different "sub-type" classifications of depressions react differently to the treatment with anti-depressive compounds (Drugs 4, 361, (1972)).

The now clinically used anti-depressive compounds influence to a different extent the re-uptake of amines in the neurons: desmethylimipramine and protriptyline have mainly a blocking effect on the cell membrane of noradrenergic neurons, while imipramine and amitriptyline in addition inhibit the re-uptake of serotonine by serotonergic neurons (J. Pharm. Pharmacol. 20 150 (1968), J. Pharmacol. 4 135 (1968)).

There are a number of brain processes in which serotonine and noradrenaline have opposite activities (Ann. N.Y. Acad. Sci. 66 631 (1957); Adv. Pharmacol 6B 97 (1968); and Jouvet in Van Praag: Brain and Sleep 1974). In the medicinal treatment of depressive patients, the intensification of the function of one amine might result in a decrease of the function of the other amine.

As a means to elevate the mood of depressive patients, there exists, on the basis of the above, a significant need of pharmacy, for a compound whose activity mainly consists of blocking the cell membrane of the serotonergic neurons (Van Praag, Psyche aan banden, (1974), i.e. whose activity is mainly based on the potentiation of serotonine.

It was found that the novel compounds of formula I

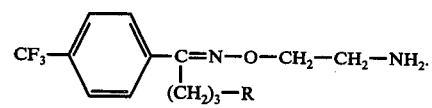

and salts thereof with pharmaceutically acceptable acids fulfil the imposed requirements. The compounds provide a very powerful serotonine potentiation which is associated with a weaker noradrenaline potentiation. The compounds do not have an activity component based on monoamine oxidase inhibition, are substantially free from side effects such as stomach ulceration and bronchoconstriction and have a very low toxicity.

In Formula I, R has the following meanings: a cyano group, a cyano methyl group, a methoxymethyl group of an ethoxymethyl group.

While it is surprising that a very strong serotonine potentiation was found for the novel compounds of the present invention when compared with known compounds from British Patent Specification No. 1,205,665 which known compounds only show an anti-depressive activity based on noradrenaline potentiation and/or on MAO inhibition, even more surprising is the selectivity by which the compounds according to the invention potentiate serotonine (expressed in the low ratios $ED_{50}$ serotonine potentiation/$ED_{50}$ noradrenaline potentiation (serot./noradr.)).

The compounds according to the invention were compared with the most closely structurally related known compounds. The results of this examination are recorded in the following table.

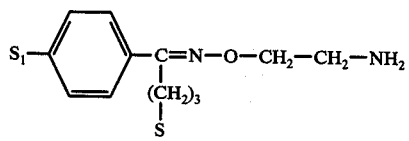

| $S_1$ | Compound S | | noradr. pot. | serot. pot. | serot noradr. | MAO inhib. | stomach ulcer. | bronch. constr. |
|---|---|---|---|---|---|---|---|---|
| $CF_3$ | CN | * | 47 | 8.6 | 0.18 | >215 | — | — |
| $CF_3$ | $CH_2CN$ | * | >215 | 30 | <0.14 | >215 | — | — |
| $CF_3$ | $(CH_2)OCH_3$ | ** | 107 | 36 | 0.3 | >215 | — | — |
| $CF_3$ | $(CH_2)OC_2H_5$ | *** | 43 | 37 | 0.85 | >215 | — | — |
| $CF_3$ | $C_2H_5$ | * | ? | 32 | ? | >215 | — | + |
| Cl | H | * | 6.2 | 22 | 3.5 | 52 | + | — |
| Cl | $CH_3$ | * | 5.6 | 12 | 2.1 | >215 | + | — |

-continued $$S_1-\bigcirc-\underset{\underset{S}{\overset{(CH_2)_3}{|}}}{C}=N-O-CH_2-CH_2-NH_2$$

| $S_1$ | Compound S | noradr. pot. | serot. pot. | serot noradr. | MAO inhib. | stomach ulcer. | bronch. constr. |
|---|---|---|---|---|---|---|---|
| Cl | $C_2H_5$ | * 1.9 | 14 | 7.4 | >215 | + | + |

* HCl salt;
** maleate 1:1;
*** fumarate 1:1.

In this table, the numbers $ED_{50}$ denote values expressed in mg/kg; with the exception of the column serot./noradr. which states ratios of $ED_{50}$ values. These ratios which are smaller to much smaller than 1 for the compounds according to the invention are indicative of the selectivity of the compounds. This is in strong contrast with the numbers which were found for the known compounds. It is to be noted that for the compound $S_1=CF_3$, $S=C_2H_5$, no $ED_{50}$ value for the noradrenaline potentiation could be measured. As a matter of fact, the results obtained with this substance vary so considerably that no estimation of the presumable $ED_{50}$ value can even be given.

The second known compound ($S_1=Cl$; $S=H$) has a significant MAO inhibition, while it holds for all the four known compounds that they give stomach ulceration and/or broncho-constriction.

The data recorded in the table were determined in the following tests.

The noradrenaline potentiation was determined in the tetrabenazine test. In this test, a quantity of the compound to be tested was administered orally to five male albino mice. After 45 minutes the animals were injected subcutaneously with 80 mg/kg of tetrabenzine. After another 45 minutes the degree of ptosis was determined and compared with the ptosis of animals which have received tetrabenazine alone. The $ED_{50}$ was determined from the results.

The serotonine potentiation was determined in the 5-hydroxytryptophan test. For this purpose the compounds to be tested were administered orally in a series of dosages to isolated male albino mice (5 mice per dosage) 1 hour prior to intraperitoneal administration of 150 mg/kg of dl-5-hydroxytryptophan. 30 Minutes after this threshold dosage the mice were observed individually and the following parameters were scored: stereotypical shaking of the head, spreading of the hindlegs, tremor, tendency to flee, lordosis, clonic stamping with the frontlegs. The $ED_{50}$ value was calculated from the results.

The monoamino oxidase (MAO) inhibiting effect was determined in experiments in which a quantity of the compound to be tested was administered orally to five male albino mice. One hour later the animals were injected subcutaneously with tryptamine hydrochloride in a quantity of 250 mg/kg. This quantity did not cause mortality in animals which did not receive the compound to be tested, but did cause morality in animals to which an active substance has been administered. Eighteeen hours after the administration of tryptamine hydrochloride it was determined how many treated animals had died. The $ED_{50}$ was determined from the results.

By means of the method by Metyšovà, Arzneimittelforschung 13 - 1039 (1963) it was determined whether the oral administration of 200 mg of a compound to be tested causes stomach ulceration.

By means of the method by Konzett-Rössler, Arch. Exp. Path. Pharmakol 195 71 (1940) it was investigated whether a compound to be tested causes broncho-constriction after intravenous administration of 3 mg. In this method reduction of the breathing function as a result of broncho-constriction is expressed in a smaller volume of air taken in.

On the basis of their properties the compounds of formula I and their salts are particularly suitable for use in the treatment of depressive patients, in particular to elevate their mood.

This applies in particular to 5-methoxy-4'-trifluoromethylvalerophenone O-(2-aminoethyl) oxime and salts thereof with pharmaceutically acceptable acids, such as the maleate 1:1.

This compound was tested clinically in a number of very heavily depressive patients which had previously been treated unsuccessfully with commerically available anti-depressive agents. The patients reacted particularly well to the compounds according to the invention, while a significantly strong elevation of mood occurred.

The quantity, the frequency and route by which the substances according to the invention are administered may vary for each individual patient and also in accordance with the nature and the severity of the disturbances to be treated. In general, adults will receive a daily dose of from 25–500 mg orally. As a rule, a daily oral dosage of 50 to 200 mg will suffice.

The compounds are preferably used in the form of pills, tablets, coated tablets, capsules, powders, injection liquids, and the like. The compounds may be processed to such compositions according to methods which are known per se.

The invention therefore also relates to compositions having a compound of formula I or a salt thereof as the active constituent with a pharmaceutically acceptable acid and to methods to prepare said compositions, for example, by mixing the active compound with or dissolving it in solid or liquid pharmaceutical carrier materials.

As examples of pharmaceutically acceptable acids with which compounds of formula I can form salts may be mentioned: inorganic acids, for example hydrochloric acid, sulphuric acid, nitric acid and organic acids, such as citric acid, fumaric acid, tartaric acid, benzoic acid, maleic acid and the like.

The compounds of formula I and their salts may be prepared according to methods which are known for the preparation of this type of compounds and according to methods analogous thereto.

The invention also relates to the preparation of the compound.

They can be obtained inter alia by converting a compound of formula II

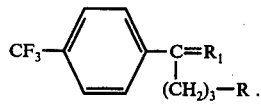

with the compound of formula III

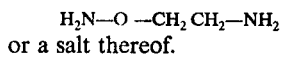

$H_2N-O-CH_2CH_2-NH_2$ or a salt thereof.

In these formulae R has the same meaning as in formula I and $R_1$ is an oxygen atom, an oxime group or an alkylene dioxy group, for example, ethylene dioxy. The reaction is preferably carried out in an inert solvent, for example, an alcohol, dioxan, dimethylformamide, tetrahydrofuran or a mixture thereof, at temperatures between room temperature and the boiling point of the mixture and possibly in the presence of an acid binder, for example, pyridine.

Another method consists of a reaction between a compound of formula IV

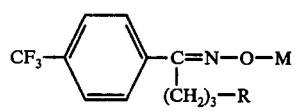

in which M is a hydrogen atom or an alkali metal atom and R has the same meaning as in formula I and a compound of formula V $Hal-CH_2-CH_2-NH_2$ or a salt thereof, wherein Hal is a halogen atom preferably a chlorine atome or a bromine atom.

The reaction is preferably carried out in an inert solvent, for example, alcohols, ethers or dimethyl formamide. In the case in which M is a hydrogen atom, an acid binder, for example an alcoholate, is preferably added. As a rule the reaction temperature is between 0° and 50° C.

The compounds can also be obtained by reacting a compound of formula VI

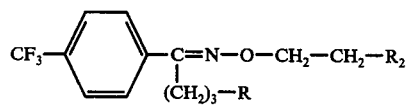

wherein R has the same meaning as in formula I and $R_2$ is a mesyloxy group or a tosyloxy group, with ammonia. The reaction is preferably carried out in an inert solvent, for example an alcohol, usually at temperatures between room temperature and 150° C.

The compounds of formula VI can be prepared by converting a compound of formula IV with ethylene oxide in ethanol and in the presence of an alcoholate at temperatures up to 60° C. The reaction product is then converted with tosyl chloride or mesyl chloride into a compound of formula VI, for example, in an inert solvent, for example methylene chloride.

Another method of preparing the compounds of formula I consists of a reaction of a compound of formula VII

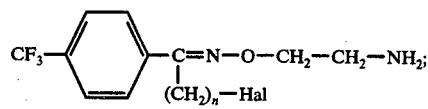

with a compound of formula VIII M'R', in which formulae n has the value 3 or 4, Hal is a halogen atom, preferably a chlorine atom or a bromine atom, M' is an alkali metal atom and R' is a cyano group or a methoxy group or an ethoxy group.

This reaction is preferably carried out in an inert solvent, for example ethanol, dimethyl sulfoxide, dimethyl formamide and the like, at temperatures between 0° and 70° C. The compounds of formula I in which R contains an oxygen atom can also be obtained by converting a compound of formula IX

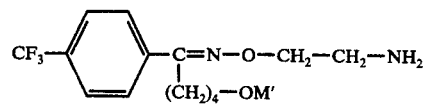

with a compound of formula $R_3$-R". In these formulae M' is an alkali metal atom, $R_3$ is a halogen atom, for example a chlorine atom or a bromine atom, or a group $(SO_4)_{1/2}$ and R" is a methyl group or an ethyl group.

The reaction is preferably carried out in an inert solvent, for example toluene or dimethyl formamid. As a rule the reaction takes place at a temperature between 0 and 80° C.

The compounds of formula I wherein R contains an oxygen atom can also be prepared by reducing a compound of formula XI

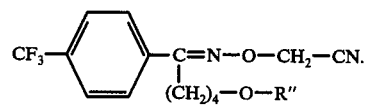

In this formula, R" is a methyl group or an ethyl group. The reaction may be carried out with a reduction agent, for example, metal hydride, for example, lithium aluminium trimethoxy hydrid in a solvent for example tetrahydrofuran, dioxan and the like at a temperature between 0 and 25° C.

The compounds of formula I can also be obtained by hydrolysing a compound of formula XII

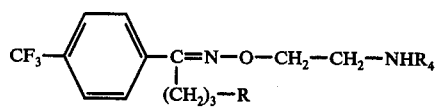

wherein $R_4$ is a protective group, for example, a trityl group. The reaction may be carried out in a water-mixed inert solvent, in acid conditions, at a temperature between room temperature and 100° C, The invention will now be described in greater detail with reference to the following examples.

EXAMPLE 1

5-Methoxy-4'-trifluoromethylvalerophenone O-(2-aminoethyl) oxime maleate (1:1).

20.4 Mmol (5.3 g) of 5-methoxy-4'-trifluoromethylvalerophenone (melting point 43°–44° C), 20.5 mmol (3.1 g) of 2-aminooxyethylaminedihydrochloride and 10 ml of pyridine were refluxed for 15 hours in 20 ml of absolute ethanol. After evaporating the pyridine and the ethanol in vacuo, the residue was dissolved in water. This solution was washed with petroleum ether and 10 ml of 50% sodium hydroxide solution were then added. Then three extractions with 40 ml of ether were carried out. The ether extract was washed successively with 20 ml of 5% sodium bicarbonate solution and 20 ml of water. After drying on sodium sulphate, the ether layer was evaporated in vacuo. Toluene was then evaporated another three times (to remove the pyridine) and the oil thus obtained was dissolved in 15 ml of absolute ethanol. An equimolar quantity of maleic acid was added to said solution and the solution was then heated until a clear solution was obtained. The ethanol was then removed in vacuo and the residue was crystallized from 10 ml of acetonitrile at +5° C. After sucking off and washing with cold acetonitrile, it was dried in air. The melting point of the resulting title compound was 120°–121.5° C.

EXAMPLE 2

5-Ethoxy-4'-trifluoromethylvalerophenone O-(2-aminoethyl) oxime fumarate (1:1).

The title compound having a melting point of 150°–150.5° C was obtained in an identical manner from 5-ethoxy-4'-trifluoromethylvalerophenone with the difference that fumaric acid was added to the solution in ethanol.

EXAMPLE 3

4-Cyano-4'-trifluoromethylbutyrophenone O-(2-aminoethyl) oxime hydrochloride.

5.6 Mmol (1.35 g) of 4-cyano-4'-trifluoromethylbutyrophenone, 5.6 mmol (0.84 g) of 2 aminooxyethylamine dihydrochloride and 0.8 ml of pyridine were refluxed in 20 ml of absolute ethanol for 2.5 hours. The processing was equal to that of example 1. The resulting free base was dissolved in absolute ethanol and an equivalent quantity of 2N alcoholic hydrochloric acid was added. The ethanol was then removed in vacuo and the residue was crystallized twice from ethanol/ether (1:5). The melting point of the resulting title compound was 136°–136.5° C.

EXAMPLE 4

5-Cyano-4'-trifluoromethylvalerophenone O-(2-aminoethyl) oxime hydrochloride.

The title compound having a melting point of 142°–143.5° C was obtained in an identical manner from 5-cyano-4'-trifluoromethylvalerophenone (51°–52° C).

EXAMPLE 5

4-Cyano-4'-trifluoromethylbutyrophenone O-(2-aminoethyl) oxime hydrochloride.

8.0 Mmol (4.3 g) of 4-cyano-4'-trifluoromethylbutyrophenone O-(2-tritylaminoethyl) oxime (melting point 87°–88° C) were dissolved in 40 ml of 90% acetic acid. After standing at room temperature for three days, this reaction mixture was evaporated to dryness in vacuo after which the residue was dissolved in 50 ml of ether. The resulting solution was extracted with 40 ml of 0.2N hydrochloric acid and this extract was extracted with 50 and 25 ml of methylene chloride, respectively, after rendering alkaline with 10 ml of 2N sodium hydroxide solution. The resulting solution was dried (sodium sulphate) and evaporated in vacuo. The residue was dissolved in 80 ml of absolute ethanol and acidified with an equivalent quantity of 2N alcoholic hydrochloride acid. After evaporating the ethanol, two crystallizations were carried out from ethanol/ether (1:5). Melting point 136°–136.5° C.

EXAMPLE 6

5-Methoxy-4'-trifluoromethylvalerophenone O-(2-aminoethyl) oxime maleate (1:1).

5.0 Mmol of 5-methoxy-4'-trifluoromethylvalerophenone oxime (melting point 41.5°–42.5° C), 5.2 mmol (0.60 g) of 2-chloro-ethyl-amine-hydrochloride and 0.7 g of KOH powder were added in this sequence and while stirring at 10° C to 12.5 ml of dimethylformamide (DMF). After stirring at room temperature for 2 days, DMF was removed in vacuo, the residue was brought in water and then 2N hydrochloric acid was added until pH=3. The remaining oxime was removed by means of ether, after which 15 ml of 2N sodium hydroxide solution were added. Three extractions with ether were then carried out. The collected ether layers were washed with a 5% sodium bicarbonate solution and dried on sodium sulphate. After removing the ether in vacuo, the residue was dissolved in absolute ethanol to which an equimolar quantity of maleix acid was added. There was heated until a clear solution was obtained, after which the ethanol was removed in vacuo. The residue was crystallized from acetonitrile. The resulting title compound had a melting point of 120°–121.5° C.

EXAMPLE 7

5-Methoxy-4'-trifluoromethylvalerophenone O-(2-aminoethyl) oxime maleate (1:1)

a. 26 Mmol (1.15 g) of ethylene oxide were led into a suspension of 15.5 mmol (4.3 g) of 5-methoxy-4'-trifluoromethylvalerophenone-oxime (melting point 41.5°–43.5° C) in 25 ml of absolute ethanol in which first 0.03 g or Li had been dissolved, while stirring at 55° C and by means of a flow of nitrogen. Then stirring was continued for another hour at 60° C. After the addition of 0.3 ml of acetic acid, the ethanol was distilled off in vacuo and the residue was purified chromatographically over silica gel with $CH_2Cl_2$ as an eluent. After evaporating the solvent, the O-(2-hydroxy-ethyl) oxime was obtained as an oil.

b. 2.23 Ml of triethylamine were added to a solution of 11 mmol (3.6 g) hereof in 60 ml of methylene chloride while stirring at −5° C to 0° C and 12 mmol (0.9 ml) of mesylchloride were then added dropwise in approximately 20 minutes. Stirring was continued at 0° C for another 30 minutes, the mixture was then washed with successively ice water (4x), with a 5% sodium bicarbonate solution of 0° C (1x) and with a saturated NaCl solution of 0° C (2x). After drying on sodium sulphate at 5° C, the $CH_2Cl_2$ was distilled off in vacuo at a bath temperature of 40 to 60° C. The O-(2-mesyloxy-ethyl) oxime was obtained in this manner.

c. A mixture of 8 mmol (3.2 g) hereof in 30 ml of methanol which contained 233 mmol (4.0 g) of NH₃ was kept at 100° C in an autoclave for 16 hours. After cooling the methanol was removed in vacuo, the residue was stirred with 50 ml of 2N sodium hydroxide solution and extracted with ether. The ether layer was washed with a 5% sodium bicarbonate solution. After drying on sodium sulphate and distilling off the ether in vacuo, it was dissolved in absolute ethanol to which an equimolar quantity of maleic acid was added. The ethanol was evaporated in vacuo and the residue taken up in acetonitrile from which the title compound crystallized.

EXAMPLE 8

5-Ethoxy-4'-trifluoromethylvaleophenone O-(2-aminoethyl) oxime fumarate (1:1)

7 Mmol (2.2 g) of 5-ethoxy-4'-trifluoromethylvalerophenone-ethylene-ketal and 7 mmol (1.0 g) of 2 aminooxyethylamine dihydrochloride were refluxed in 10 ml of methanol for 4 hours. After evaporating the methanol in vacuo, the residue was dissolved in water and washed two times with ether. 3 Ml of 50% sodium hydroxide solution were then added and three extractions with CH₂Cl₂ were carried out. This extract was washed with 5% sodium bicarbonate solution (1x) and water (1x). The solution was then dried on sodium sulphate and the CH₂Cl₂ was distilled off in vacuo. The residue was taken up in absolute ethanol and acidified with an equimolar quantity of fumaric acid . The title compound crystallized from the solution. Melting point 150°–150.5° C.

EXAMPLE 9

5-Cyano-4'-trifluoromethylvalerophenone O-(2-aminoethyl) oxime hydrochloride.

10 Mmol (4.3 g) of 5-chloro-4'-trifluoromethylvalerophenone O-(2-aminoethyl) oxime maleate (1:1) (melting point 121.5°–122.5° C) were dissolved in 50 ml of water. 5 Ml of 50% sodium hydroxide solution at 0° C were added. Three extractions with 25 ml of CH₂Cl₂ were then carried out and this extract was washed with 5% sodium bicarbonate solution (1x) and water (1x). The solution was then dried on sodium sulphate and the CH₂Cl₂ was distilled off in vacuo. The residue was dissolved in 10 ml of dimethylsulfoxide (DMSO) and 25 mmol (1.2 g) of sodium cyanide were then added. The suspension was heated at a temperature of 50° to 70° C for 3 hours and then cooled to room temperature. Then there was diluted with 100 ml of 0.5 N sodium hydroxide solution and three extractions with 40 ml of ether were carried out. The ether extract was washed with water (1x), dried on sodium sulphate and evaporated in vacuo. The residue was purified chromatographically over silica gel with ethanol/ammonia (95:5) as an eluent. After evaporating the solvents, the residue was dissolved in absolute ethanol and acidified with ethanolic hydrochloric acid. After crystallization from ethanol/ether (1:3) the title compound having a melting point of 142°–143.5° C was obtained.

EXAMPLE 10

5-Ethoxy-4'-trifluoromethylvalerophenone O-(2-aminoethyl)oxime fumarate (1:1)

12 Mmol (5.1 g) of 5-chloro-4'-trifluoromethylvalerophenone O-(2-aminoethyl) oxime maleate (1:1) (melting point 121.5°–122.5° C) were added to a solution of 240 mgat. (5.5 g) of sodium in 100 ml of absolute ethanol. The mixture was heated at 70° C for 8 hours followed by neutralization at 0° C with alcoholic hydrochloric acid and the sodium chloride was filtered off. The alcohol was distilled off in vacuo and the residue was dissolved in water. 5 Ml of 50% sodium hydroxide solution were added to this solution and three extractions with 40 ml of ether were then carried out. The ether extract was washed with 5% sodium bicarbonate solution (1x) and with water (1x), followed by drying on sodium sulphate. The ether was distilled off in vacuo and the residue was dissolved in absolute ethanol. The solution was acidified with an equimolar quantity of fumaric acid. The title compound crystallized from the solution. Melting point 105°–105.5° C.

EXAMPLE 11

5-Ethoxy-4'-trifluoromethylvalerophenone O-(2-aminoethyl) oxime fumarate (1:1).

24.7 Mmol (1.00 ml) of methanol and 3 ml of tetrahydrofuran (THF) were added to 7.8 mmol (0.3 g) of LiAlH₄ in 10 ml of THF while stirring and cooling in ice water for 3 minutes. A solution of 1.15 mmol of 5-ethoxy-4'-trifluoromethylvalerophenone O-(cyanomethyl) oxime was then added while stirring and cooling for ten minutes. After stirring the reaction mixture at 5° C for another 3 hours it was decomposed with 1.0 ml of water. The formed hydroxides were sucked off, washed with chloroform and the filtrate was evaporated to dryness in vacuo. The resulting base was dissolved in absolute ethanol and an equimolar quantity of fumaric acid was added. The mixture was heated until a clear solution was obtained. The solvent was removed, the residue was taken up in ethanol/acetonitrile 1:1. The title compound crystallized. Melting point 150°–150.5° C.

EXAMPLE 12

TABLET 50 mg of 5-methoxy-4'-trifluoromethylvalerophenone O-(2-aminoethyl) oxime maleate (1:1).
335 mg of lactose
60 mg of potato starch
25 mg of talc
5 mg of magnesium stearate
5 mg of gelatine

EXAMPLE 13

SUPPOSITORY 50 mg of 5-methoxy-4'-trifluoromethylvalerophenone O-(2-aminoethyl) oxime maleate (1:1)
1500 mg of suppository mass.

EXAMPLE 14

INJECTION LIQUID 25 g of 5-methoxy-4'-trifluoromethylvalerophenone O-(2-aminoethyl)oxime maleate (1:1).
1.80 g of methyl p-hydroxybenzoate
0.20 g of propyl o-hydroxybenzoate
9.0 g of sodium chloride
4.0 g of poly(oxyethylene)₂₀ sorbitan monooleate
water to 1000 ml.

What is claimed is:

1. Oxime ether compounds of the formula

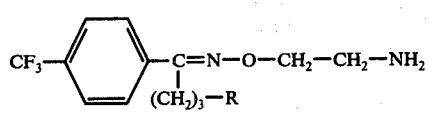
(I)

and salts thereof with pharmaceutically acceptable acids, in which formula R is a cyano group, a cyanomethyl group, a methoxymethyl group or an ethoxymethyl group.

2. The 5-Methoxy-4'-trifluoromethylvalerophenone O-(2-aminoethyl) oxime and salts thereof with pharmaceutically acceptable acids of claim 1.

3. The 5-Ethoxy-4'-trifluoromethylvalerophenone O-(2-aminoethyl) oxime and salts thereof with pharmaceutically acceptable acids of claim 1.

4. An oxime compound of the formula:

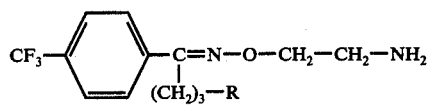

wherein R is cyano or cyanomethyl.

5. The 4-Cyano-4'-trifluoromethylbutyrophenone O-(2-aminoethyl) oxime and salts thereof with pharmaceutically acceptable acids of claim 4.

6. The 5-Cyano-4'-trifluoromethylvalerophenone O-(2-aminoethyl) oxime and salts thereof with pharmaceutically acceptable acids of claim 4.

7. An antidepressive composition comprising a compound of claim 1 in an antidepressively effective amount and a pharmaceutically acceptable carrier therefore.

8. A method of treating patients suffering from depression comprising administering to said patients a composition of claim 7 in an antidepressively effective amount.

* * * * *

UNITED STATES PATENT AND TRADEMARK OFFICE
CERTIFICATE OF CORRECTION

PATENT NO. : 4,085,225
DATED : April 18, 1978
INVENTOR(S) : HENDRICUS BERNARDUS ANTONIUS WELLE ET AL It is certified that error appears in the above-identified patent and that said Letters Patent are hereby corrected as shown below:

Col. 2, line 36, change "of" to --or--

Col. 6, line 31, change "179" to --1/2--

Signed and Sealed this

Eighth Day of May 1979

[SEAL]

Attest:

RUTH C. MASON
Attesting Officer

DONALD W. BANNER
Commissioner of Patents and Trademarks

UNITED STATES PATENT AND TRADEMARK OFFICE

CERTIFICATE EXTENDING PATENT TERM
UNDER 35 U.S.C. § 156

PATENT NO.      : 4,085,225

ISSUED          : April 18, 1978

INVENTOR(S)     : Hendricus Bernardus Antonius Welle et al.

PATENT OWNER :  Duphar International Research B.V.

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of

TWO YEARS from the original expiration date of the patent, April 18, 1995, with all rights pertaining thereto as provided by 35 U.S.C. § 156(b).

I have caused the seal of the Patent and Trademark Office to be affixed this 3rd day of June 1996.

Bruce A. Lehman
Assistant Secretary of Commerce and
  Commissioner of Patents and Trademarks